(12) United States Patent
Ostertag et al.

(10) Patent No.: US 6,589,331 B2
(45) Date of Patent: Jul. 8, 2003

(54) SOFT IRON PIGMENTS

(75) Inventors: Werner Ostertag, Grunstadt (DE); Stefan Trummer, Nuremberg (DE); Frank Henglein, Nuremberg (DE); Klaus Greiwe, Lauf (DE)

(73) Assignee: Eckart GmbH & Co. KG, Fürth (DE)

( * ) Notice: Subject to any disclaimer, the term of this patent is extended or adjusted under 35 U.S.C. 154(b) by 0 days.

(21) Appl. No.: 10/103,839

(22) Filed: Mar. 25, 2002

(65) Prior Publication Data

US 2002/0134282 A1 Sep. 26, 2002

(30) Foreign Application Priority Data

Mar. 23, 2001 (DE) ......................... 101 14 445

(51) Int. Cl.$^7$ ................................. C09C 1/22
(52) U.S. Cl. ................. 106/460; 106/403; 106/415; 106/456
(58) Field of Search ................ 106/403, 415, 106/460, 456

(56) References Cited

FOREIGN PATENT DOCUMENTS

| DE | 44 14 079 A1 | 10/1995 |
|---|---|---|
| DE | 44 19 173 A1 | 12/1995 |
| DE | 44 37 753 A1 | 4/1996 |
| DE | 694 13 083 T2 | 2/1999 |
| DE | 198 20 225 A1 | 11/1999 |
| EP | 0 673 980 A2 | 9/1995 |
| EP | 0 959 108 A1 | 11/1999 |

*Primary Examiner*—C. Melissa Koslow
*Assistant Examiner*—Shalie Manlove
(74) *Attorney, Agent, or Firm*—Browdy and Neimark, P.L.L.C.

(57) ABSTRACT

The present invention deals with metal oxide coated, flake shaped soft iron pigments. The characteristic feature is a reflector substrate, which is produced by deformation of reduced carbonyl iron powder. The pigments are colorful, display metallic luster and a high magnetic permeability. They can be oriented in the medium by means of an external magnetic field. The novel pigments find use in the decorative and/or functional field, particularly in lacquers, paints, plastics, in printing, in glass, ceramics and in cosmetics.

9 Claims, No Drawings

SOFT IRON PIGMENTS

BACKGROUND OF THE INVENTION

1. Field of the Invention

The present invention is directed to flake shaped, metal oxide coated soft iron pigments.

2. Background Art

Colored effect pigments that display a metallic luster have been the object of intense research and development efforts for many years because of their special optical qualities, particularly because of their brilliancy. Effect pigments are pigments of a flake shape that display a direct reflection and only little scattering. In addition to reflection properties, they may also display interference properties and must be oriented in a preferred direction by a method based on the given application. The special feature of all applications that are pigmented with effect pigments is the pronounced angle-dependence of the optical appearance. The particle size of effect pigments considerably exceeds that of coloring pigments. The preferred particles that find the most application have sizes between 5 and 50μ and a diameter-to-thickness ratio of 30–150. Flakes with a diameter up to 250μ are used in a few fields of application. The conceptions regarding the ideal shape of metallic effect pigments, in practice, are based on the so-called "silver dollar", a largely spheroidal aluminum flake that has few scattering centers. The present invention describes effect pigments that have the layer sequence metal oxide—iron—metal oxide. In the category of the metal oxide coated iron pigments only few developments have become known to date. They are essentially concerned with iron pigments that display temper colors. The term temper colors refers to interference reflection phenomena that result from the oxidation of the surface of metal particles. Known metal pigments that display temper colors are the superficially oxidized brass pigments that are on the market in various shades of color depending on the thickness of the oxide film.

DE 4419 741 describes iron pigments that display temper colors. The colored effect pigments with a metallic luster are produced by atomizing molten iron, grinding the resulting granular iron, and subsequently heating the flake shaped particles to 200–500° C. in the presence of atmospheric oxygen. When heated in air, an oxide layer forms on the surface of the iron particles and temper colors appear in the color tones gold, red violet and blue. The production of colored iron pigments with metallic luster is described very similar in EP 673980. There, too, granular iron is first produced by atomizing molten iron. Subsequent wet grinding of the granular iron and subsequent heating of the ground products at 350° C. produce the temper colors gold, copper, violet and blue in that order. The sequence of colors requires a time period of only 1–4 minutes. The shortcomings of iron pigments with temper colors and the method of their production are manifold. The most significant shortcoming is the low reproducibility of the color hues. Even a slight change in the thickness of the iron oxide coating is enough to produce different interference reflection colors, and the oxide layer that is produced by oxidation of the iron surface is also not conclusively defined regarding its composition ($Fe_2O_3/Fe_3O_4$). Since pure iron in a fine distribution reacts pyrophoric, the difficulties in adjusting discrete color hues become greater as the particle size of the iron flakes decreases. EP 673980 thus describes only the production of relatively large iron flakes with temper colors (70–80% of the particles are between 100–300μ). Further deficits of the described methods for producing the above iron-based effect pigments already result in the atomizing step. When molten iron is atomized, the granular iron is obtained relatively large-grained and with not very homogeneously distributed particle sizes. Since a particle size range of 5–50μ is preferred in effect pigments, the iron particles that are produced by atomizing must not only be deformed but also reduced in size. This is very expensive. Furthermore, the reactivity of the iron flakes significantly increases with their reduction in size.

In view of the difficulties involved in the production of suitable iron substrates and their susceptibility to oxidization, a number of developments in the past have dealt with the metal oxide coating of corrosion and oxidization resistant special steel flakes. Special steel or "stainless steel" refers to iron alloys with 18–30% Cr, 0–8% Ni, also Mo, Cu, V and C. Stainless steel flakes are on the market for applications in heavy corrosion proofing. Even though iron is the main component of the special steel flakes—which frequently results in the catchy but misleading term iron flakes—developments in metal oxide coatings of special steel or stainless steel flakes are not in competition with the object of the present invention. The reasons are as follows: special steel alloys have different optical constants than iron. Since the optical constants of the reflector material largely determine the overall optical appearance of the pigments, one must distinguish between special steel and iron. Special steel furthermore lacks the ductility of iron, which is why usually only relatively thick flakes with little coverage are available for coatings.

Special steel flakes, in contrast to iron flakes, are for the most part produced by metal-cutting processes. Lastly, special steel lacks the ferromagnetism that is characteristic for iron and which represents the cause for the orientability of metal oxide coated iron flakes with the aid of an external magnetic field. The applications that deal with the coating of special steel or stainless steel flakes are listed below, to complete the picture:

DE 41 043 10.3 describes oxide-coated flake shaped pigments that are produced wet-chemically by coating stainless steel flakes with iron oxide and titanium oxide. The pigments display a steel gray or black gray body color and interference colors. The production of titanium dioxide coated stainless steel flakes is described similarly in JP 10/110 113. WO 00/43 457 describes the production of $Fe_2O_3$, $TiO_2$ and $ZrO_2$ coated effect pigments, the metallic core material is preferably composed of titanium, tantalum, zircon, stainless steel or Hastelloy (a nickel alloy).

Alternative methods for producing metal oxide coated iron pigments by PVD methods and subsequent reduction in size of the films that are prepared in the vacuum are conceivable. However, so far no products with the layer sequence metal oxide—iron—metal oxide ("three-layer combo" with iron reflector layer) have become known that are produced according to this method. The high cost would likely conflict with an implementation of this concept on an industrial scale.

From this follows that the development of effect pigments on the basis of iron depends to a significant degree on making suitable metal substrates available. Of the pigment developments described so far, none is able to meet the requirements in the decorative and functional fields.

SUMMARY OF THE INVENTION

It was the object of the present invention to develop novel, colorful effect pigments with metallic luster for decorative and functional fields of application. The novel pigments were intended to stand out by their brilliancy and their orientability with the aid of an external magnetic field. They were to have a high covering power and particle sizes preferably in the range of 5–36μ. The novel pigments were furthermore supposed to be stable in slightly alkaline conditions, as they are found in many water lacquers.

This object was met with the use of highly pure reduced carbonyl iron powder, which is commercially available in a spherical particle shape and narrow particle size distribution in various particle sizes from 1–10μ (suppliers: BASF AG, Ludwigshafen, or ISP, Wayne, N.J.) This powder, which is mechanically soft and ductile because of its purity, is gently ground and subsequently subjected to the oxide coating. The oxide coating may take place via wet-chemical deposition processes or via CVD methods in the fluidized bed. It has proven advantageous if the flake-like deformed soft iron powder is superficially passivated. Oxides that are particularly suitable for the oxide coating are highly refracting, transparent or partially transparent oxides, such as $TiO_2$, $TiO_{2-x}$, $Fe_2O_3$, $Fe_2O_{3-x}$ or the mixed phases of hematite with $Al_2O_3$, $Cr_2O_3$ and/or $Mn_2O_3$.

As a starting product for producing the substrates for the novel colored effect pigments, soft iron powder as it is obtained in the reduction of carbonyl iron powder was discovered. Carbonyl iron powder is produced by decomposition of iron carbonyl vapor and is a specialty product of the chemical industry. It is obtained in round particles with average particle sizes of 1–10μ in an extremely narrow particle size distribution and has an initial iron content of approximately 96–97%. Contaminants are carbon, oxygen and nitrogen. The particles that are obtained initially are mechanically hard. By reductive treatment at an increased temperature the mechanically hard powder can be transformed into soft iron powder, which has an iron content of >99.0% or, better, >99.5%. The particles of the highly pure reduced carbonyl iron powder are soft and easily deformed by mechanical means (Technisches Merkblatt der BASF, M 5686 d). Both non-reduced as well as reduced carbonyl iron powder is commercially available in various average particle sizes (1–10μ). With reduced carbonyl iron powder it is possible to produce the iron substrates of the novel colorful effect pigments with metallic luster, which have high covering powder, magnetic permeability, and good stability in slightly alkaline media. Similar to fine-particle highly pure granular aluminum, which is used to produce the so-called "silver dollar" pigments, reduced carbonyl iron powder with average particle sizes of 1–10μ, because of its high ductility, is particularly suitable for the production of flake shaped iron substrates. The deformation into flake shapes takes place by grinding in ball mills, for which small grinding media (1–5 mm) are preferred. The grinding may take place both by wet grinding with the use of white spirit or also by dry grinding. To prevent cold welding, a lubricant, such as oleic acid, stearic acid or phosphonium compounds, are advantageously added in small quantities (0.1–3 percent by weight). The particle diameters and shape factor (diameter-to-thickness ratio) of the desired iron substrates can be controlled within wide margins via the grinding time and selection of the average particle diameter of the starting material. The grinding generally lasts 1–12 hours. After the grinding the iron flakes with metallic luster already reveal a thin oxide-containing passivation layer, which is formed through reaction of the iron surface with atmospheric oxygen or ubiquitous water. It has proven advantageous to improve the passivation of the soft iron flakes by chromatization, phophatization, nitration and other passivation methods that are known in the industry. The passivation results in the formation of a very thin barrier layer on the surface of the soft iron particles. Due to its small thickness (<20 nm) it virtually does not become optically noticeable. The flake shaped soft iron pigments have a darker metallic luster than, for example, aluminum pigments. The reflection power of iron is in the visible wavelength range between 50 and 60%.

The coating of the surface of the flake shaped soft iron particles with a metal oxide layer may consist of one or more oxides of the transitional elements. Preferred oxides are those of titanium, of iron, and of mixed phases of oxides of iron with those of chromium and/or aluminum and/or manganese. Particularly preferred among the iron oxides is hematite ($\alpha$—$Fe_2O_3$). The higher the refractive index of the deposited oxide, the lower the coating thicknesses that are necessary to produce interference phenomena.

If the process is performed wet-chemically, the hydrolysis products of soluble metal salts, such as titanyl sulfate, titanium tetrachloride, iron chloride, chromium sulfate, etc., are deposited onto the surface of the soft iron particles, which are kept in motion at an increased temperature in an aqueous medium. The deposition is followed by a filtering, rinsing, drying and calcination step. The drying and calcination must take place gently, optionally in the vacuum or under inert gas so that no oxidation of the soft iron substrates of the pigments takes place at the increased temperature. As an alternative to the wet-chemical coating, chemical vapor deposition (reactive CVD methods) may also be used to produce the metal oxide coative CVD methods) may also be used to produce the metal oxide coated soft iron pigments. In this method, vapor-state metal compounds such as iron pentacarbonyl [$Fe(CO)_5$] or $TiCl_4$ are oxidized or hydrolyzed in the gas phase and the respective resulting $Fe_2O_3$ or $TiO_2$ aerosols are deposited onto the soft iron flakes that are moved around in the gas flow at an increased temperature. In the pigment industry, fluidized beds have proven useful for CVD coatings on metal flakes (U.S. Pat. No. 4,328,042). Interference colors can be produced in a targeted manner by controlling the thickness of the coating.

An additional coating of the metal oxide coated soft iron flakes with compounds that improve the dispersibility and the orientability of the effect pigments in the medium is possible. Coatings of this type are not relevant from a coloristic point of view. Appropriate coating substances may be higher fatty acids, but also fatty acid derivatives or dicarboxylic acid derivatives, organic phosphites and phosphonium compounds, phosphoric acid esters, silanes, organic and cyclic amines, oxygen-, sulfur- or nitrogen-containing heterocycles, sulfur-nitrogen compounds of higher ketones, alcohols and aldehydes as well as mixtures of the same.

From a coloristic point of view, it is possible to produce a multitude of colorful pigment individuals with metallic luster. The given color hues and brilliancy of the products result from the optical constants of the soft iron substrates, the absorption constants and refractive index of the metal oxide coatings, and the layer thickness of the oxide layer. For the optical appearance, the layer thickness of the oxide layer is an important parameter. It becomes apparent that the metal oxide coated soft iron pigments develop interference phenomena already at relatively low layer thicknesses, as is typical for interference reflection pigments. With hematite ($\alpha$—$Fe_2$—$O_3$) coated soft iron pigments, interference can be already observed starting at a layer thickness of approximately 20 nm (yellow). With an increasing layer thickness the interference colors orange, red, violet, green and blue are obtained, which are then followed by the interference colors of the higher order. The prerequisite for easily perceptible interference colors is a high homogeneity and uniformity of the coating.

A characteristic feature of the oxide coated soft iron pigments is their high magnetic permeability. The pigments can thus easily be oriented during their application with an external magnetic field. Optically impressive light/dark patterns and color hue changes can be created in the process. In the past it was often attempted to generate magnetically orientable pigment particles through ferromagnetic coatings (Fell-containing $Fe_2O_3$, $Fe_3O_4$, $\gamma$—$Fe_2O_3$). This was done at the expense of optically dull and esthetically not very impressive surfaces. The utilizable magnetic power of such pigments was furthermore considerably less than in the case of the highly permeable soft iron pigment substrates for which there are no restrictions regarding the coating with optically attractive metal oxides.

The field of application for the inventive pigments is the decorative field, as well as the functional field. The pigments are used in the lacquer, in paints, plastics, for printing, in glass, ceramics and in cosmetics. In the functional sector, the special magnetic properties, those of the electrical conductivity, the ability to absorb radar waves, or the ability to shield against electromagnetic waves, are utilized. Security printing may be named as an example in which importance is placed on the decorative and functional properties of the novel effect pigments. In this field, the printing of the inventive pigments on banknotes permits an optically impressive, unmistakable marking of the security print on one hand, and money counting machines in banks that operate based on the principle of induction, are able to read the magnetically highly permeable soft iron substrate of the pigment particles.

The following experiments serve as examples to illustrate the invention.

EXAMPLE 1 A

Production of Flake Shaped Soft Iron Powder 400 g of "reduced carbonyl iron powder" from firm BASF A.G. Ludwigshafen/Rhein, Germany, which carries the designation SQ, is entered together with 0.75 liters white spirit and 7 g stearic acid into a ball mill of dimensions 30 cm×25 cm which is half-filled with 4 mm diameter steel grinding balls.

The SQ carbonyl iron powder, according to its specifications, has an iron content of >99.5% Fe and particles in the order of magnitude of 4–6$\mu$. The contaminants are listed as carbon >0.06%, nitrogen <0.01% and oxygen <0.4% (Technical Leaflet M 5686 e, March 1995). This is then ground for 4.5 hours at 70 revolutions per minute. After completion of the grinding, the mill is emptied, the ground powder is separated from the grinding means, filtered, washed with white spirit and subsequently dried in the vacuum drying chamber at 70° C.

The obtained flake shaped soft iron pigment displays a high metallic luster and high magnetic permeability. The average particle size of the product is determined by means of Cilas measurements (laser beam refraction) as 15$\mu$. Scanning electron microscope images show that the particles have a pronounced flake shape and a diameter-to-thickness ratio of approximately 60:1.

EXAMPLE 1 B

Passivation of the Flake Shaped Soft Iron Substrate by $CrO_3$ Oxidation 300 g of the flake shaped soft iron substrates produced in Example 1A are entered into a solution of 600 g ethyl glycol, 400 g water and 30 g $CrO_3$ and stirred at 70° C. for one hour.

The flake shaped soft iron substrates are then filtered off, washed with ethanol and dried in the vacuum drying chamber at 100° C.

EXAMPLE 1 C

Passivation of the Flake Shaped Soft Iron Substrates by $SiO_2$ 300 g of the flake shaped soft iron substrates produced in Example 1 A are dispersed in 2 liters of water and adjusted to a pH of 10 with NaOH. 6 g $SiO_2$ are then added as sodium silicate (sodium water glass). The pH is brought to 4 by adding 0.1 n $H_2SO_4$ solution over a period of two hours while stirring.

The $SiO_2$ passivated product is washed with water and dried in the vacuum drying chamber at 80° C.

EXAMPLE 2

Oxide Coating of Flake Shaped Soft Iron Substrate 64.3 g of the soft iron substrates produced according to Example 1 C and passivated with $SiO_2$, are entered into a 250 ml rotating flask in 122 g deionized water. The pH is adjusted to 3.2 with HCl. The suspension is heated to 75° C. After the temperature has been reached, a 28% $FeCl_3$ solution is added at a metering rate of 0.11 ml/min over a period of 11 hours.

During this time the pH is held constant by adding 25% NaOH. The suspension is stirred for five hours, then filtered, washed with deionized water and dried in the vacuum drying chamber at 95° C. over four hours.

The obtained pigment displays an orange-yellow interference color and metallic luster. Dispersed into an alkyde melamine resin lacquer (draft DIN 53 283) and applied on a black/white cardboard with a spiral doctor blade in 100 $\mu$m wet film thickness, the pigment shows pronounced angle-dependent reflection. It can be oriented via an external magnetic field.

EXAMPLE 3

Oxide Coating of Flake Shaped Soft Iron Substrate 500 g of the passivated soft iron pigment produced according to Example 1 B are suspended in 3 liters of water and heated to 75° C. By adding HCl the pH is adjusted to 3.3. A 40% $FeCl_3$ solution is then added at a metering rate of 90 ml/h while stirring. The pH is maintained at 3.3 by adding 15% NaOH solution. Altogether 450 iron chloride solution are added. The coated flakes are filtered, washed with water and dried in the vacuum drying chamber at 70° C. Afterwards they are calcinated at 300° C. for a period of 20 min in a revolving tube through which nitrogen is passed.

The obtained pigment has a metallic brilliant red interference color and high covering power. Due to its magnetic properties it can easily be oriented with an external magnetic field. Analyses show that the interference-capable iron oxide layer is roughly 40 nm thick.

EXAMPLE 4

$Fe_2O_3$ Coating in the Fluidized Bed 500 g of flake shaped soft iron pigment as it is described in Example 1, A+B, is entered into a fluidized bed reactor of glass. The fluidized bed reactor is heatable with infrared radiators, has a conical vortex gas inlet in its lower portion, mechanically cleanable filter bags on top, and two lateral nozzles that are mounted at a two-thirds height. It has an inside diameter of 6 cm and a height of 90 cm. An air/nitrogen mixture in the ratio of 1:6 is introduced through the lower opening of the fluidized bed reactor. The gas volume is increased until the bulk material of flake shaped soft iron powder swells and the particles are moving in the bed in a floating manner. With the aid of the infrared radiators the temperature in the interior of the fluidized bed is raised to 200° C. Iron pentacarbonyl vapor, $Fe(CO)_5$ is subsequently introduced via the lateral nozzles with the aid of a carrier gas. This is done in such a way that 50 g/h iron pentacarbonyl are vaporized in an evaporator and transported into the reactor with the aid of 200 liters $N_2$/h (at 20° C.). The oxidation product from the reaction of iron pentacarbonyl and atmospheric oxygen spontaneously deposits onto the fluidized soft iron flakes. Over a period of eight hours the iron oxide coated soft iron pigment displays the interference colors yellow, orange, red, violet, green-gray, blue-gray, yellow, orange, red, violet, one after another. After termination of the coating, the product is cooled in the reactor and removed from the same. Smaller quantities of the product may also be removed during the coating process through a cooled tube.

The products, which are removed in half-hour intervals, display, without exception, metallic luster and interference colors. The yellow, orange and red interference colors are of particular brilliancy. Due to the inherent magnetic properties of the soft iron substrates, the iron oxide coated soft iron pigments can easily be oriented in the lacquer. The pigments that are applied in the lacquer have a distinct angle-dependent reflection. X-rays show that the coating consists of $\alpha$—$Fe_2O_3$. Analyses show that the red interference pigments of the $2^{nd}$ order (end of the coating time) have an iron oxide thickness of approximately 120 nm.

What is claimed is:

1. Flake shaped, metal oxide coated soft iron pigments, wherein the flake shaped pigment substrates are obtained from reduced carbonyl iron powder by deformation, and the oxide coating consists of one or more transparent or selectively absorbing metal oxides.

2. Flake shaped, metal oxide coated iron pigments according to claim 1, wherein the flake shaped soft iron pigments are passivated prior to the coating.

3. Flake shaped, metal oxide coated iron pigments according to claim 1, wherein the oxide coating is deposited either wet-chemically or by chemical vapor deposition.

4. Flake shaped, oxide coated iron pigments according to claim 1, wherein the oxide coating has a thickness that permits interference reflection.

5. Flake shaped oxide coated iron pigments according to claim 1, wherein the oxide coating consists of iron oxide and/or iron oxide-based mixed phases.

6. Flake shaped oxide coated iron pigments according to claim 1, wherein the pigments incorporate additional coatings that improve the dispersion and orientation behavior.

7. Flake shaped, metal oxide coated soft iron pigments according to claim 1, obtained by grinding.

8. In a method for pigmenting a lacquer, paint, plastic, glass, ceramic, cosmetic or printing ink, comprising adding a pigment thereto, the improvement wherein said pigment is an oxide coated iron pigment according to claim 1 providing a magnetically permeable effect.

9. In a printing method comprising printing with a pigment, the improvement wherein said pigment is a flake shaped, metal oxide coated iron pigment in accordance with claim 1.

* * * * *